US011657734B2

(12) United States Patent
Lander

(10) Patent No.: US 11,657,734 B2
(45) Date of Patent: May 23, 2023

(54) SYSTEM AND METHOD FOR ACOUSTIC WAVE INDUCED TRAUMATIC BRAIN INJURY

(71) Applicant: Cell Surgical Network Corporation, Rancho Mirage, CA (US)

(72) Inventor: Elliot B. Lander, Rancho Mirage, CA (US)

(73) Assignee: CELL SURGICAL NETWORK CORPORATION, Rancho Mirage, CA (US)

(*) Notice: Subject to any disclaimer, the term of this patent is extended or adjusted under 35 U.S.C. 154(b) by 141 days.

(21) Appl. No.: 17/339,493

(22) Filed: Jun. 4, 2021

(65) Prior Publication Data
US 2021/0398456 A1    Dec. 23, 2021

Related U.S. Application Data

(63) Continuation of application No. 15/994,497, filed on May 31, 2018, now abandoned.

(60) Provisional application No. 62/624,093, filed on Jan. 30, 2018.

(51) Int. Cl.
G09B 23/30    (2006.01)
A61B 5/00     (2006.01)
G10K 11/26    (2006.01)
G09B 23/28    (2006.01)
G09B 19/00    (2006.01)
G10K 9/12     (2006.01)

(52) U.S. Cl.
CPC ............ G09B 23/30 (2013.01); A61B 5/4064 (2013.01); G09B 19/00 (2013.01); G09B 23/28 (2013.01); G10K 11/26 (2013.01); G10K 9/12 (2013.01)

(58) Field of Classification Search
CPC ........ G09B 23/30; G09B 19/00; G09B 23/28; G10K 11/26; G10K 9/12; A61B 5/4064
USPC ........................................................ 434/267
See application file for complete search history.

(56) References Cited

U.S. PATENT DOCUMENTS

| 6,901,933 B2 | 6/2005 | Meythaler et al. |
| 2004/0035433 A1 | 2/2004 | Meythaler et al. |
| 2013/0186173 A1 | 7/2013 | Ravin et al. |
| 2014/0107523 A1 | 4/2014 | Petraglia et al. |

OTHER PUBLICATIONS

Alder, J.; Fujioka, W.; Lifshitz, J.; Crockett, D.P.; Thakker-Varia, S. Lateral fluid percussion: Model of traumatic brain injury in mice. J. Vis. Exp. 2011, 22, e3063.
Babaee, A.; Eftekhar-Vaghefi, S.H.; Asadi-Shekaari, M.; Shahrokhi, N.; Soltani, S.D.; Malekpour-Afshar, R.; Basiri, M. Melatonin treatment reduces astrogliosis and apoptosis in rats with traumatic brain injury. Iran. J. Basic Med. Sci. 2015, 18, 867-872.
Beauchamp, K.; Mutlak, H.; Smith, W.R.; Shohami, E.; Stahel, P.F. Pharmacology of traumatic brain injury—where is the "golden bullet"? Mol. Med. 2008, 14, 731-740.
(Continued)

Primary Examiner — Michael C Grant
(74) Attorney, Agent, or Firm — Foley & Lardner LLP

(57) ABSTRACT

Disclosed herein are systems and methods of generating traumatic brain injury. More specifically, the present disclosure relates to acoustic systems and methods for inflicting traumatic brain injury and developing an animal model of traumatic brain injury.

20 Claims, 10 Drawing Sheets

(56) References Cited

OTHER PUBLICATIONS

Beaumont, A.; Marmarou, A.; Hayasaki, K.; Barzo, P.; Fatouros, P.; Corwin, F.; Marmarou, C.; Dunbar, J. The permissive nature of blood brain barrier (bbb) opening in edema formation following traumatic brain injury. Brain Edema XI 2000, 76, 125-129.
Berman, et al., Validation of Acoustic Wave Induced Traumatic Brain Injury in Rats. Brain Sciences. Jun. 2, 2017, pp. 1-14, vol. 7, No. 59.
Berman, Sean et al., Effective Treatment of Traumatic Brain Injury in Rowett Nude Rats with Stromal Vascular Fraction Transplantation, MDPI, Jun. 18, 2018, 10 pages.
Budde, M.D.; Shah, A.; Mccrea, M.; Cullinan, W.E.; Pintar, F.A.; Stemper, B.D. Primary blast traumatic brain injury in the rat: Relating diffusion tensor imaging and behavior. Front. Neurol. 2013, 4, 154.
Cernak, I. Animal models of head trauma. Neurotherapeutics 2005, 2, 410-422.
Cole, J.T.; Yarnell, A.; Kean, W.S.; Gold, E.; Lewis, B.; Ren, M.; Mcmullen, D.C.; Jacobowitz, D.M.; Pollard, H.B.; O'Neill, J.T.; et al. Craniotomy: True sham for traumatic brain injury, or a sham of a sham? J. Neurotrauma 2011, 28, 359-369.
Cristian, A. Blast-related mild traumatic brain injury: Mechanisms of injury and impact on clinical care. Mt. Sinai J. Med. 2009, 76, 111-118.
Cunon, V.A.; Putukian, M.; Boyer, C.; Dewttwiler, A. A diffusion tensor imaging study on the white matter skeleton in individuals with sports-related concussion. J. Neurotrauma 2001, 28, 189-201.
Dixon, C.E.; Clifton, G.L.; Lighthall, J.W.; Yaghmai, A.A.; Hayes, R.L. A controlled cortical impact model of traumatic brain injury in the rat. J. Neurosci. Methods 1991, 39, 253-262.
Elliott, M.B.; Jallo, J.J.; Barbe, M.F.; Tuma, R.F. Hypertonic saline attenuates tissue loss and astrocyte hypertrophy in a model of traumatic brain injury. Brain Res. 2009, 1305, 183-191.
Flierl, M.A.; Stahel, P.F.; Beauchamp, K.M., Morgan, S.J., Smith, W.R., Shohami, E. Mouse closed head injury model induced by a weight-drop device. Nat. Protoc. 2009, 4, 1328-1337.
Friedland, D. Improving the classification of traumatic brain injury: The May classification system for traumatic brain injury severity. Spine 2013, doi:10.4172/2165-7939.S4-005.
Ghadiri, T.; Sharifzadeh, M.; Khodagholi, F.; Mousavi, S.M.M.; Hassanzadeh, G.; Zarrindast, M.-R.; Gorji, A. A novel traumatic brain injury model for induction of mild brain injury in rats. J. Neurosci. Methods 2014, 233, 18-27.
Henninger, N.; Dützmann, S.; Sicard, K.M.; Kollmar, R.; Bardutzky, J.; Schwab, S. Impaired spatial learning in a novel rat model of mild cerebral concussion injury. Exp. Neurol. 2005, 195, 447-457.
Hoge, C.W.; McGurk, D.; Thomas, J.L.; Cox, A.L.; Engel, C.C.; Castro, C.A. Mild traumatic brain injury in U.S. soldiers returning from Iraq. N. Engl. J. Med. 2008, 358, 453-463.
Jorden, B.D. Chronic traumatic brain injury associated with boxing. Semin Neurol. 2000, 20, 179-185.
Kerr, Z.Y.; Harmon, K.J.; Marshall, S.W.; Proescholdbell, S.K.; Waller, A.E. The epidemiology of traumatic brain injuries treated in emergency departments in North Carolina 2010-2011. NC Med. J. 2014, 75, 8-14.
Kolb, B.; Sutherland, R.J.; Whishaw, I.Q. A comparison of the contributions of the frontal and parietal association cortex to spatial localization in rats. Behav. Neurosci. 1983, 97, 13-27.
Langlois, J.; Rutland-Brown, W.; Wald, M. The epidemiology and impact of traumatic brain injury: A brief overview. J. Head Trauma Rehabil. 2006, 21, 375-378.
Malkesman, O.; Tucker, L.B.; Ozl, J.; McCabe, J.T. Traumatic brain injury—Modeling neuropsychiatric symptoms in rodents. Front. Neurol. 2013, 4, 157.
Marar, M.; McIlvain, N.M.; Fields, S.K.; Comstock, R.D. Epidemiology of concussions among United States high school athletes in 20 sports. Am. J. Sports Med. 2012, 40, 747-755.
McKee, A.; Robinson, M. Military-related traumatic brain injury and neurodegeneration. Alzheimers Dement. 2014, 10, 242-253.
Meyer, P.G.; Ducrocq, S.; Carli, P. Pediatric neurologic emergencies. Curr. Opin. Criti. Care 2001, 7, 81-87.
Mishra, V.; Skotak, M.; Schuetz, H.; Heller, J.; Chandra, N. Primary blast cause mild, moderate, sever and lethal TBI with increasing blast overpressures: Experimental rat injury model. Sci. Rep. 2016, 6, 26992.
Morehead, M.; Bartus, R.T.; Dean, R.L.; Miotke, J.A.; Murphy, S.; Sall, J.; Goldman, H. Histopathologic consequences of moderate concussion in an animal model: Correlations with duration of unconsciousness. J. Neurotrauma 1994, 11, 657-667.
Mukherjee, S.; Zeitouni, S.; Cavarsan, C.F.; Shapiro, L.A. Increased seizure susceptibility in mice 30 days after fluid percussion injury. Front. Neurol. 2013, 4, 28.
Nakagawa, et al., Shock wave-induced brain injury in rat: Novel traumatic brain injury animal model. Acta Neurochir Suppl. 2008, pp. 421-424, No. 102.
Namjoshi, D.R.; Good, C.; Cheng, W.H.; Panenka, W.; Richards, D.; Cripton, P.A., Wellington, C.L. Towards clinical management of traumatic brain injury: A review of models and mechanisms from a biomechanical perspective. Dis. Models Mech. 2013, 6, 1325-1338.
Ozen, I.; Boix, J.; Paul, G. Perivascular mesenchymal stem cells in the adult human brain: A future target for neuroregeneration? Clin. Transl. Med. 2012, 1, 30.
Petraglia, A.L.; Dashnaw, M.L.; Turner, R.C.; Bailes, J.E. Models of mild traumatic brain injury: Translation of physiological and anatomic injury. Neurosurgery 2014, 75, S34-S49.
Raghupathi, R.; Graham, D.I.; Mcintosh, T.K. Apoptosis after tramatic brain injury. J. Neurotrauma 2000, 17, 927-938.
Redish, A.D.; Touretzky, D.S. The role of the hippocampus in solving the Morris water maze. Neural Comput. 1998, 10, 73-111.
Rinder, L.; Olsson, Y. Vascular Permeability changes in experimental brain concussion. Acta Pathol. Microbiol. Scand. 2009, 72, 350-352.
Shultz, S.; MacFabe, D.; Foley, K.; Taylor, R.; Cain, D. A single mild fluid percussion injury induces short-term behavioral and neuropathological changes in the Long-Evens rat: Support for an animal model of concussion. Behav. Brain Res. 2011, 224, 326-335.
Thompson, H.J.; LeBold, D.G.; Marklund, N.; Morales, D.M.; Hagner, A.P.; McIntosh, T.K. Cognitive evaluation of traumatically brain-injured rats using serial testing in the Morris water maze. Restor. Neurol. Neurosci. 2006, 24, 109-114.
Watts, L.T.; Long, J.A.; Chemello, J.; Koughnet, S.V.; Fernandez, A.; Huang, S.; Shen, Q.; Duong, T.Q. Methylene blue is neuroprotective against mild traumatic brain injury. J. Neurotrauma 2014, 31, 1063-1071.
Williams, A.J.; Hartings, J.A.; Lu, X.-C.M.; Rolli, M.L.; Dave, J.R.; Tortella, F.C. Characterization of a new rat model of penetrating ballistic brain injury. J. Neurotrauma 2005, 22, 313-331.
Wojcik, B.E.; Stein, C.R.; Bagg, K.; Humphrey, R.J.; Orosco, J. Traumatic brain injury hospitalizations of U.S. army soldiers deployed to Afghanistan and Iraq. Am. J. Prev. Med. 2010, 38, 108-116.
Xiong, Y.; Mahmood, A.; Chopp, M. Animal models of traumatic brain injury. Nat. Rev. Neurosci. 2013, 14, 128-142.
Yu, S.; Kaneko, Y.; Bae, E.; Stahl, C.; Wang, Y.; van Loveren, H.; Sanberg, P.; Borlongan, C. Severity of controlled cortical impact traumatic brain injury in rats and mice dictates degree of behavioral defects. Brain Res. 2009, 1287, 157-163.

SYSTEM AND METHOD FOR ACOUSTIC WAVE INDUCED TRAUMATIC BRAIN INJURY

CROSS-REFERENCE TO RELATED APPLICATION

This application is a continuation of U.S. patent application Ser. No. 15/994,498, filed May 31, 2018, which claims the benefit of and priority to U.S. Provisional Patent Application No. 62/624,093, filed Jan. 30, 2018, the contents of which are incorporated herein by reference in their entireties.

TECHNICAL FIELD

The present disclosure generally relates to systems and methods of generating traumatic brain injury. More specifically, the present disclosure relates to acoustic systems and methods for inflicting traumatic brain injury and developing an animal model of traumatic brain injury.

BACKGROUND

Traumatic brain injury (TBI) is a severe injury affecting an estimated 3.8 million Americans and 10 million people globally each year with many more incidents going unreported. TBI occurs when a blow to the head displaces the brain beyond the blood-brain barrier resulting in small lesions in the white matter in mild TBI, to more extreme subdural hematoma and damaged affected neurons in moderate and severe TBI. When the brain is displaced beyond the cerebrospinal fluid it sits in, it collides into the bony skull and can cause blood vessels in the brain to rupture in moderate and severe TBI. The disruption in the cerebral vasculature prevents adequate blood flow, depleting neurons of oxygen and essential nutrients. The neurons eventually die via apoptosis, and this form of neurodegeneration can be directly associated with both the short-term symptomatic effects (e.g., poor motor coordination, severe headaches, and complete loss of consciousness) and the long-term effects (e.g., memory loss, depression and suicidality) of TBI.

Military personnel in combat scenarios exposed to extreme overpressures associated with explosions can experience TBI even though they may not come into direct contact with any solid objects. The pressure from these acoustic blasts emits forces equal to or greater than the physical force required for a mild TBI. Blast TBI (bTBI) can often go undetected initially, but the typical short-term and long-term symptoms of TBI can surface during the same timeline. bTBI has been coined the "signature injury" of the recent wars in Iraq and Afghanistan with 22% of military personnel in these venues experiencing the adverse effects of bTBI. Although the means of acquisition are different, the mechanisms and physiology of acoustic-produced TBI are similar to concussions that are often observed in athletics, automobile accidents, and everyday mishaps.

Experimental impact models have been developed to mimic human TBI in rodent models as well as other animals such as ferrets; cats, monkeys, and swine. Five standard impact models are generally used in research and include the fluid percussion impact (FPI), controlled cortical impact (CCI), penetrating ballistic-like brain injury (PBBI), Marmarou's weight drop, and blast brain injury models.

The open head models for TBI include FPI, CCI, and PBBI, all of which involve a craniotomy before administering the TBI. These methods may accurately model TBI specifically within the brain, but the surrounding biological chemistry may be altered due to craniotomy surgery and associated comprehensive damage. Furthermore, these open-head penetrating models may not be appropriate for administering regenerative stem cell therapy to treat TBI, For example, mesenchymal stem cells (MSCs) have shown the capacity to differentiate into neuronal cells. Major damage to the neighboring skull via craniotomy and destruction of surrounding tissue release a cascade of inflammatory cytokines, significantly reducing the ability of the MSCs to differentiate into neuronal cells.

Closed head TBI models include Marmarou's weight drop and blast exposure. The Marmarou's weight drop model is the most prevalent closed head technique used to study cellular and molecular responses to TBI. However, the precision of this technique depends on the animal's neck musculature and may not be very reproducible with high mortality rates around 44%. High-speed cameras also show that there may be a secondary, unintentional rebound injury in other regions of the brain after the initial impact of the weight drop. The blast exposure models detonate a small explosive device or compressed air in a tube containing an animal in order to study the shockwave effect on the brain from peak pressure 154 to 340-kPa at different time intervals. However, the ensuing shockwave has been shown to cause injuries to air-filled organs not associated with TBI.

Brain injury severity is commonly classified as mild, moderate, and severe, which is based on the 15-point Glasgow Coma Scale (GCS) in humans. The GCS scores from 13-15 is categorized as a mild TBI, 9-12 is moderate TBI, and 3-8 is severe TBI. There are generally six categories of symptoms that are currently used to clinically diagnose mTBI (mild traumatic brain injury): alteration, duration of loss of consciousness, Glasgow Coma. Scale (30 min post injury with a score of 13-15), post-traumatic amnesia, focal, and brain imaging. In animal models, the primary injury of a mTBI causes the mechanical disruption of the tissue, and the pathology of the secondary injury may ultimately cause further tissue damage and atrophy as seen in the single mild TBI in a FPI animal study by Shultz (Shultz, S.; MacFabe, D.; Foley, K.; Taylor, R.; Cain, D. A single mild fluid percussion injury induces short-term behavioral and neuropathological changes in the Long-Evens rat: Support for an animal model of concussion. *Behav. Brain Res.* 2011, 224, 326-335), and mild TBI in a CCI animal study by Yu (Yu, S.; Kaneko, Y.; Bae, E.; Stahl, C.; Wang, Y.; van Loveren, H.; Sanberg, P.; Borlongan, C. Severity of controlled cortical impact traumatic brain injury in rats and mice dictates degree of behavioral defects. *Brain Res.* 2009, 1287, 157-163).

SUMMARY

In one aspect, the present disclosure provides a method of simulating traumatic brain injury (TBI) in a non-human animal model, the method comprising administering one or more acoustic waves to the brain of the animal with an acoustic wave generator, thereby resulting in brain trauma. In some embodiments, a single acoustic wave is administered to the brain of the animal. In some embodiments, the acoustic wave is administered at a pressure of 1.0-5.0 bar. In some embodiments, the acoustic wave is administered to one or more brain regions. In some embodiments, the brain region is the frontal motor cortex. In some embodiments, the non-human animal exhibits one or more of impaired cognitive function or impaired motor coordination resulting from the brain trauma. In some embodiments, the non-human animal model is a rodent.

In one aspect, the present disclosure provides a non-human animal model of traumatic brain injury (TBI), wherein one or more acoustic waves are administered to the brain of the animal with an acoustic wave generator, and wherein the one or more acoustic waves induces brain trauma. In some embodiments, a single acoustic wave is administered to the brain of the animal. In some embodiments, the acoustic wave is administered at a pressure of 1.0-5.0 bar. In some embodiments, the acoustic wave is administered to one or more brain regions. In some embodiments, the brain region is the frontal motor cortex. In some embodiments, the non-human animal model is a rodent. In some embodiments, the animal exhibits cognitive impairment resulting from the brain trauma. In some embodiments, the animal exhibits impaired motor skills resulting from the brain trauma.

In one aspect, the present disclosure provides a system comprising an acoustic wave generator configured to produce acoustic waves resulting in brain trauma in a non-human animal. In some embodiments, a single acoustic wave is administered to the brain of the animal. In some embodiments, the acoustic wave is administered at a pressure of 1.0-5.0 bar. In some embodiments, the acoustic wave is administered to one or more brain regions. In some embodiments, the brain region is the frontal motor cortex.

The technology described and claimed herein has many attributes and embodiments including, but not limited to, those set forth or described or referenced in this brief summary. It is not intended to be all-inclusive and the technology described and claimed herein is not limited to or by the features or embodiments identified in this brief summary, which is included for purposes of illustration only and not restriction. Additional embodiments may be disclosed in the detailed description below.

BRIEF DESCRIPTION OF THE DRAWINGS

FIG. 4A and FIG. 4C show indentation and fragmentation of the cortex where TBI was administered while FIG. 4B and FIG. 4D show intact, generally unaffected tissue. In addition, the cells shown in FIG. 4A and FIG. 4C are more sparsely detected, suggesting neurodegeneration and disruption of neural pathways in these animals. All photomicrographs in FIGS. 4A-4D were taken at 40× magnification.

FIG. 5A shows the TBI-targeted left frontal cortex and FIG. 5B shows the contralateral intact right cortex at the same stereologic section. Indentation and damage of the cortex can be easily seen in the TBI-damaged hemisphere (40× magnification). FIG. 5C and FIG. 5D are higher magnification photos (100× magnification) taken from the boxed regions (FIG. 5C from the upper box, and FIG. 5D from the lower box) of FIG. 5A. These images show the presence of condensed dark cells, neuroprotective astrocytes, and granulated cells, which are likely macrophages that have phagocytized blood products. The boxes in FIG. 5C highlight the condensed dark cells, and the arrows in FIG. 5D highlight granulated cells, likely macrophages that have phagocytized blood products.

FIG. 6A shows no damage from an untreated, control rat (0 bar). FIG. 6B shows slight damage to the outer cortex (3.4 bar). FIG. 6C and FIG. 6D show the deeper penetrating impact delivered by the 4.2 and 5.0 bar. The dotted lines show examples of the infarct boundaries traced by locating the perimeter of condensed dark cells used to calculate the expanse of the area damaged. All images in FIGS. 6A-6D were taken at 40× magnification.

FIG. 8A is a chart showing the percent change in motor skills in a comparison between three groups: Group 1 was treated with SVF the day of TBI, Group 2 was treated with SVF 3 days post-TBI, and Group 3 (control) was treated with Lactated Ringer's solution the day of TBI. Behavioural testing was observed for 14 days post-TBI. N=6 for each treatment; p<0.01. FIG. 8B is a chart showing the percent change in memory in a comparison between three groups. Group 1 was treated with SVF the day of TBI. Group 3 was treated with Lactated Ringer's solution the day of TBI. The test was continued for 14 days. N=6 per treatment; p<0.01. Data from Group 2 rats treated with SVF 72 hours post injury is also included by not statistically significant.

DETAILED DESCRIPTION

Figure 1:
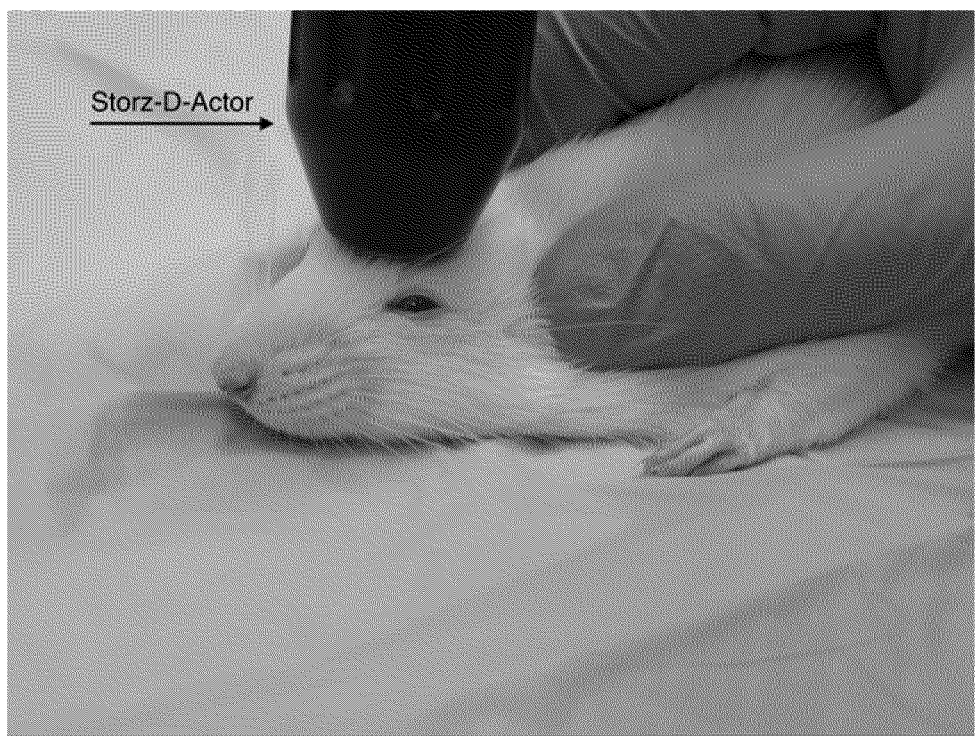
FIG. 1 is a picture showing the placement of the Storz-D-Actor (D20-S 20 mm radial head applicator) being applied to a rat brain. The Storz-D-Actor was held at 90° to the surface as the energy is directed straight down through the left frontal cortex (approximately +3.0 anterior to bregma).

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this present technology belongs.

I. Definitions

The following terms are used herein, the definitions of which are provided for guidance.

As used in this specification and the appended claims, the singular forms "a", "an" and "the" include plural referents unless the content clearly dictates otherwise. For example, reference to "a cell" includes a combination of two or more cells, and the like.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the terms "subject" and "patient" are used interchangeably. In some embodiments, that subject is a non-human animal. For example, animals may be used as analogs for human traumatic brain injury. The animal used in the model may be any mammal. For example, the mammal may be a rodent (e.g., mice, rats, guinea pigs, hamsters).

As used herein, a "traumatic injury" is any injury that has the potential to cause serious tissue damage, disability, prolonged disability, and/or death in the subject that has experienced the injury. Traumatic injuries include, but are not limited to, blast injuries (e.g., resulting from exposure to overpressures associated with explosions or acoustic waves passing through the brain) blunt injuries, sports- and/or recreation-related injuries, such as concussion and subconcussion, penetrating injuries, falls, vehicle-related collisions, shaken infant syndrome, stabbing wounds, and gunshot wounds. In the context of traumatic brain injury (TBI), traumatic injuries can be categorized as mild TBI, moderate TBI, or severe TBI. Repetitive mild TBI may lead to neurological dysfunction, including syndromes such as chronic traumatic encephalopathy (CTE).

As used herein, a "traumatic brain injury" or "TBI" refers to brain injury caused by trauma (i.e., a traumatic injury as described above), in which the brain is displaced beyond the cerebral spinal fluid, often resulting in subdural hematoma, swelling, and/or cell necrosis. In some cases, the injury is direct or indirect. The signs or symptoms of TBI may appear immediately after the traumatic event or several days or weeks later. Nonlimiting examples of the signs or symptoms of TBI include: loss of consciousness for a few seconds to a few minutes, state of confusion or disorientation, headache, nausea or vomiting, fatigue or drowsiness, difficulty sleeping, sleeping more than usual, dizziness or loss of balance, poor motor coordination, sensory problems, sensitivity to light or sound, memory loss, concentration difficulty, mood changes or mood swings; depression, anxiety.

II. Traumatic Brain Injury Model

The technology of the present disclosure includes systems and methods for an acoustically produced TBI resulting in similar brain injuries and concomitant behavioral abnormalities when compared to other animal models. In some embodiments, the present disclosure provides a model for simulating TBI in animals, such as rodents, to provide an analog for analyzing TBI in humans, In some embodiments, the acoustic wave technology of the present technology can deliver a precise controlled, closed-skull TBI that can be used in a myriad of other studies, In some embodiments, the experimental model replicates the pathophysiology of TBI and provides a basis for analyzing treatment options (e.g., stem cell therapy, such as stromal vascular fraction (SW) stem cells; see FIGS. 8A and 8B).

There are at least two distinct benefits for the use of this methodology. First, as demonstrated by the experimental examples described herein, the acoustic shockwave model can be accurately calibrated to cause a range of brain damage in a specific region with reproducible results. Second, unlike previous methods, the acoustic TBI is not, invasive and can reduce potential secondary damage resulting from craniotomy surgeries in open-skull TBI. Accordingly, in some embodiments, the TBI model of the present technology does not require surgery. This approach creates a more clinically relevant model for TBI, including blast TBI (bTBI). In addition, this model allows for the analysis of multiple or repetitive brain injuries over prolonged periods of time (e.g., as a model of chronic traumatic encephalopathy (CTE)) as the subject does not require surgery and the associated surgery recovery time. Additional benefits of the present disclosure are described herein.

In some embodiments, a TBI device may include an acoustic wave generator. The TBI device may be hand-held, or alternatively, remote controlled. In some embodiments, the TBI device may be wireless or wired. In some embodiments, the TBI device may have a plurality of probes. Further, the probe size may be smaller than 20 mm or greater than 20 mm. The probe size may be selected based upon the specific application. The TBI device may allow the user to select a desired frequency and/or pressure. In some embodiments, the frequency and/or pressure of the delivered acoustic wave can be controlled or programmed. In some embodiments, a single acoustic wave pulse is administered to the subject. In some embodiments, multiple acoustic wave pulses are administered to the subject over a period of time. In some embodiments, the TBI device can deliver an acoustic wave pulse at a pressure ranging from 0.1 to 10 bar, or any range or value therein. In some embodiments, the TBI device can deliver an acoustic wave pulse at a pressure ranging from 1 to 5 bar, or any range or value therein. In some embodiments, the TBI device may deliver an acoustic wave pulse with a pressure that exceeds 5 bar. Additionally, in some embodiments, the TBI device may deliver an acoustic wave pulse with a pressure that is less than 1 bar. In some embodiments, the TBI device may deliver acoustic wave pulses at a frequency ranging from 1-21 Hz, or any range or value therein.

In some embodiments, a Storz-D-Actor device (Storz Medical AG) can be used as a TBI device to generate acoustic waves. In some embodiments, other devices may be used to generate acoustic waves. The Storz D-Actor is a device typically used in orthopedics, cardiology, urology, and aesthetic medicine to treat wide-ranging ailments utilizing its acoustic shockwave therapy.

EXAMPLES

The following examples are provided by way of illustration only and not by way of limitation. Those of skill in the art will readily recognize a variety of non-critical parameters that could be changed or modified to yield essentially the same or similar results. The examples should in no way be construed as limiting the scope of the present technology, as defined by the appended claims.

Example 1: Animal Model of Acoustic Wave Induced Traumatic Brain Injury (TBI)

This example demonstrates that the systems and methods of the present technology are capable of inducing repeatable, closed-head brain trauma in an animal model of traumatic brain injury (TBI).

Materials and Methods

Han-Wistar Rat. This experiment was performed using 60-day-old male rats (n=40). Rats were taken from the Han-Wistar rat colony maintained at California State University Northridge. All protocols utilized in this study have been approved by both Louisiana Tech University's Institutional Animal Care and Use Committee (IACUC) as well as California State University, Northridge's IACUC.

Acoustic Wave TBI Induction Device: Storz-D-Actor. The Storz-D-Actor emits a precise, automated acoustic wave that creates a microtrauma in close proximity to wherever the handheld device is directed. The apparatus can include a control unit, a pneumatic hand-held probe (tip diameter=20 mm), and a pressurized air source. The control unit can allow the user to select the frequency and pressure of the acoustic wave, ranging from 1-5 bar.

TBI Administration. Four different pressures were tested on four groups of Han-Wistar rats (n=10 per treatment) in this experiment: 0 bar (control), 3.4 bar, 4.2 bar, and 5.0 bar. To administer the brain injury, each rat was anesthetized briefly with 2.5% isoflurane and 95% $O_2$ for 45 s. After anesthetization was determined, the rat's head was stabilized and its ears pinned back using one hand while the other hand carefully positioned the hand-held probe of the Storz D-Actor on the top of the rat skull slightly posterior to the left eye, flush with the cranial epidermis (FIG. 1). After the rat was secured, a single acoustic wave pulse was directed towards the left frontal motor cortex. The animal was then immediately placed on its back, and both the direction and time it took for the animal to roll over and right itself were recorded. Control rats were anesthetized and were treated similarly with a single, control pulse of 0 bar from the Storz-D-Actor probe.

Rotarod Test. Prior to TBI treatment, all animals underwent three, nonconsecutive days of training on a rotarod (Med Associates Inc., Fairfax, Vt.) to measure the animal's motor coordination skills both before and after treatment. The rotation of the rod slowly increased (4-40 rpm) over the course of the 300 second trial. Each day, their latency times (time spent on the rotating b) were recorded for three trials and averaged. By the last day of training, all animals were able to stay on the rotarod for all tree, 300 second trials. After the TBI was administered on day 0, the rats were retested on the rotarod on days 1, 4, 7, and 10. At this point, the time on the rotarod was extended to three, 360 second trials, as the control rats' performances improved with the additional training. Latency times (seconds) for the control and treated rats to remain on the accelerating rotarod were recorded.

Water Maze Test. To test for memory impairment, a round black plastic tub (1 m diameter) divided into four quadrants was used as a water maze. The tub was filled up to 20 cm with water (approximately 19° C.), which was made opaque by using dehydrated milk powder. Above the water line, each quadrant was marked with a unique symbol using white tape. The clear platform 5 cm in diameter sat in the same location (2.5 cm below the waterline in the $3^{rd}$ quadrant) for all sessions. The rats were placed in the water facing away from the platform in the $1^{st}$ quadrant. The time (swim latency in seconds) for the rat to turn around, swim to the hidden platform and stand on top of it for a full second was recorded. Each water maze test was conducted after completion of rotarod testing. Like, the rotarod test, the animals underwent three, nonconsecutive days of training in the water maze prior to TBI treatment. Three trials were complete each day with five minutes of rest between each trial. After TBI induction, animals were retested on days 1, 4, 7, and 10. Their swim latency times were recorded for three, nonconsecutive trials and averaged.

Histological Analysis. Ten days post-TBI administration (and after the final behavioral assays were completed), all animals were anesthetized with 400 mg/kg chloral hydrate (IP). The animals were then transcardially perfused and fixed with 4% paraformaldehyde dissolved in 0.1 M phosphate buffered saline (PBS). Their brains were removed and post-fixed in 4% paraformaldehyde/0.1 M PBS for 48 hours at 4° C. The fixed brains were then placed in a solution of 20% sucrose in paraformaldehyde/0.1 M PBS for an additional 48 hours (also at 4° C.) prior to sectioning. The cerebrum was sliced on a cryostat on the coronal plane 25 μm thick at the same stereological level for all animals. The tissue was arranged on a glass slide for drying and was hydrated in 100%, 95% and then 70% ethanol baths, respectively for 2 min each before being stained in cresyl violet for 45 s. The tissue was washed in distilled water and distained in acetic formalin for 5 minutes. The tissue was then dehydrated in 95%, 100% and 100% ethanol solutions followed by xylene for 2 minutes each. To preserve the tissue, Permount was added and sealed with a cover slip. The slides were examined under microscopy for any damaged tissue, cell death and any disruption or skew from the acoustic wave induced TBI.

In addition, histological slides from the 3.4, 4.2, and 5.0 bar treatment groups were analyzed for degree of injury. The slides used for the infarct measurements were sampled from the same stereologic region of the injured frontal cortex (approximately +3.0 anterior to bregma). Quantification of the TBI infarct area was determined by the disruption of condensed dark cells. These dead cells can be easily visualized by their shrunken, condensed, dark staining nuclei and can be located along the periphery of the infarct area. The damaged cortical area surrounding the TBI was traced by following the boundary of these peripheral dark cells.

The infarct area was then quantified using SketchandCalc™ (iCalc, Palm Cost, Fla.) to measure the region of damage ($mm^2$).

Statistics. Statistical analyses were performed on the experimental groups. Repeated measure ANOVA was performed on the data collected to complete the rotarod and water maze tests. Correlation ($R^2$) values were obtained to determine if there may be a correlation between the intensity of the TBI (righting times) and subsequent reductions in motor skills and memory testing. Finally, an ANOVA was used to examine the histology data to test for significance. All values shown in each figure were means±standard errors.

Results

Immediate Post-TBI Observations. Immediately after acoustic TBI was administered to the left frontal cortex, every rat that received a 3.4, 4.2, or 5.0 bar TBI rolled and spun to its contralateral side (right) between one and four times before righting itself fully. In contrast, rats in the control group (0 bar) displayed the ability to right themselves towards the right or left side equally, often rolling back and forth. In addition, rats in the TBI test groups visually appeared to be breathing much heavier after the administration of the TBI. Breathing had slowed while chest palpitations became much more pronounced. All rats in the control group visually showed normal breathing rates after application of isoflurane anesthesia.

In addition, the amount of time the animals spent unconscious was quite variable. Overall, animals receiving TBI took longer to right than those just receiving anesthesia and control-level (0 bar) TBI. Control animals receiving anesthesia righted themselves on average in 11.6 s compared to the 3.4 bar, 4.2 bar and 5.0 bar groups which righted on average 63.9 s, 31.5 s and 39.3 s, respectively. Of the animals that received TBI, those that received a 3.4 bar bTBI consistently righted itself the slowest, almost twice that of the other two groups.

Rotarod Test to Assess Motor Skills. The animals in each TBI group were tested on the rotarod for deterioration of their motor skills post-treatment. Their results were averaged and displayed in FIG. 2. All animals in the control group were able to exceed their training level performances and were allowed to continue for an additional 60 s (up to 360 s in total time on the rotarod) throughout the course of the 10-day post-treatment study. However, each of the TBI test groups showed decreased performances in motor skills ability over the 10-day, post-TBI assay. Specifically, the 4.2 bar test group showed the most decreased ability even one day after administration of TBI, decreasing by about 23% compared to controls. The 5.0 bar test group showed a more gradual decline in motor skills ability from day 1 to day 7, declining by 23% on day 7, before showing slight improvements on day 10, down only 17.5%. Finally, the 3.4 bar test group showed initial declines of about 9% on day 1, fell further to 18% on day 4 before trending up to 4% deficits by day 7. A repeated measures ANOVA showed statistical differences (F=5.01; p<0.005) for the rotarod test between control and treatment groups. However, there were no statistical differences among the TBI experimental groups regardless of wave intensity.

The amount of time an animal spent unconscious was correlated with motor skills performance on the rotarod test. Unconsciousness time was compared with their worst performance (the shortest latency time they spent on the rotarod) independent of which day this occurred. There were no significant correlation effects observed with $R^2$ values for the 3.4 bar, 4.2 bar, and 5.0 bar, which were 0.031, 0.009 and 0.001, respectively. The $R^2$ value for the control group was 0.0517, also non-significant.

Water Maze Test to Assess Memory Impairments. To test for memory dysfunction as a symptom of TBI, animals in each treatment group (n=10 for each treatment) completed the water maze assay on pretreatment day (day 0) and then post-treatment days 1, 4, 7, and 10. The results were averaged and displayed in FIG. 3. The control group showed the most improvement in finding the hidden platform compared to the TBI experimental groups as their times improved throughout the experiment. The 3.4 bar group regressed by 21% from day 0 to day 1, but then saw increases in swim latency times regressing 61% from day 0 to day 4 and regressing 84% by day 7, before settling down 42.5% on day 10. The 4.2 bar test group also had significantly slower latency times, down 51%, one day after TBI. The 4.2 bar group recovered slightly, down only 40% by day 7; yet, on day 10, the 4.2 bar rats took even more time (66% slower) to find the hidden platform. Likewise, the 5.0 bar test group showed a slight 20% increase in swim time to find the platform on day 1. On day 4, their swim time slowed over 8 s, down 115% from baseline. From day 7 to day 10, swim times reversed similar to the 4.2 bar group, and were 33.7% slower than pretreatment values. Repeated measures ANOVA (F=2.80; p<0.05) showed significant differences between control and treated TBI groups. Similar to the rotarod assay, there were no statistical differences among the TBI experimental groups in the water maze assay regardless of wave intensity.

As with the rotarod assay, the correlation with time (s) an animal spent unconscious and their worst water maze performance (the longest time taken to find the hidden platform) on the water maze test was examined. Similar to the rotarod performance, there were no significant effects observed with the $R^2$ values for the 3.4 bar, 4.2 bar, and 5.0 bar, which respectively were 0.0002, 0.0007, and 0.1225. The $R^2$ value for the control group was 0.070 and was non-significant.

Figure 4A:
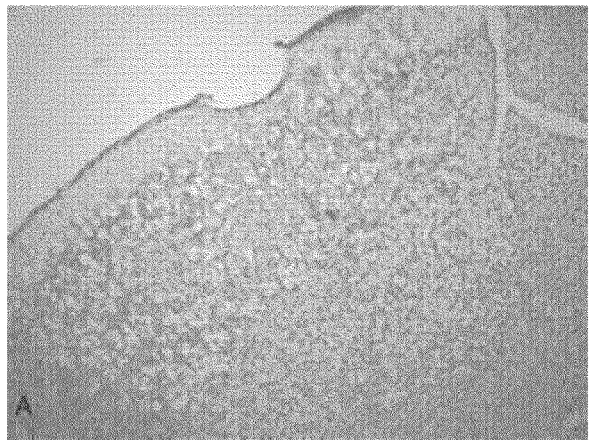
FIG. 4A-FIG. 4D are microphotographs showing the tissue from the frontal cortex visualized with cresyl violet from 60 day-old Han-Wistar rats, 10 days post-injury. Images indicate the damage from the acoustic wave 3.4 bar TBI targeted left frontal cortex as shown in the left panels (FIG. 4A and FIG. 4C) and compared with the contralateral, unaffected right frontal cortex (FIG. 4B and FIG. 4D) from the matching animals.
Figure 4B:
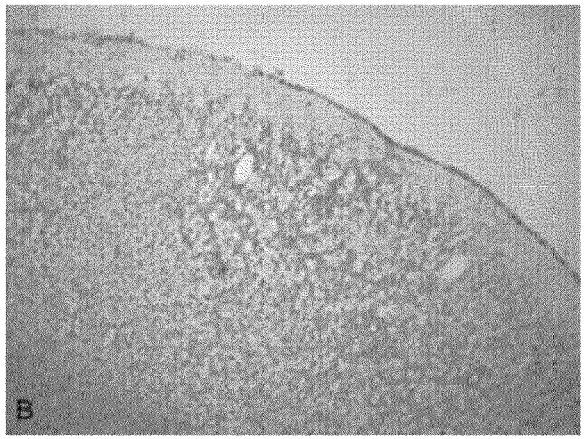
Figure 4C:
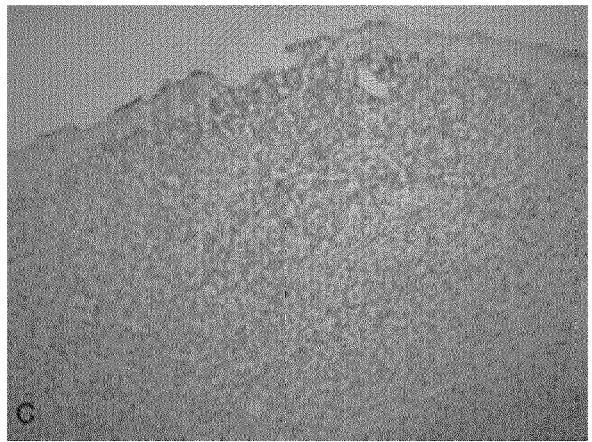
Figure 4D:
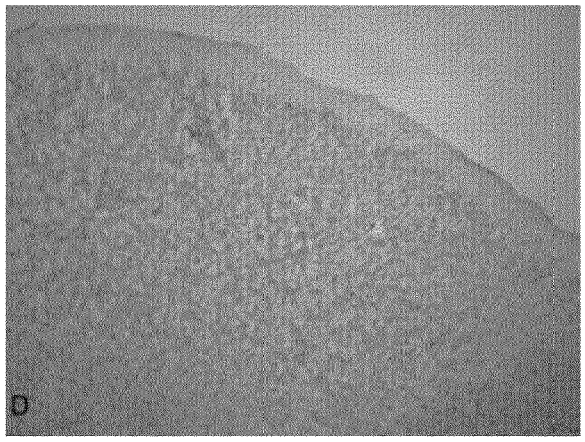

Histological Assay. Microphotographs of cresyl violet stained tissue from 3.4 bar TBI treatment (FIG. 4A and FIG. 4C) show indentation and fragmentation of the cortex exactly where the acoustic wave was administered to two separate rats. The opposing panels (FIG. 4B and FIG. 4D) show intact, generally unaffected tissue in the contralateral cortex at the same stereologic orientation (approximately +3.0 anterior to bregma). In addition, the cells in FIG. 4A and FIG. 4C appeared to be more sparsely distributed in the damaged region, suggesting neurodegeneration and disruption of neural pathways. Similar histological profiles were observed with 4.2 bar sections.

Figure 5B:
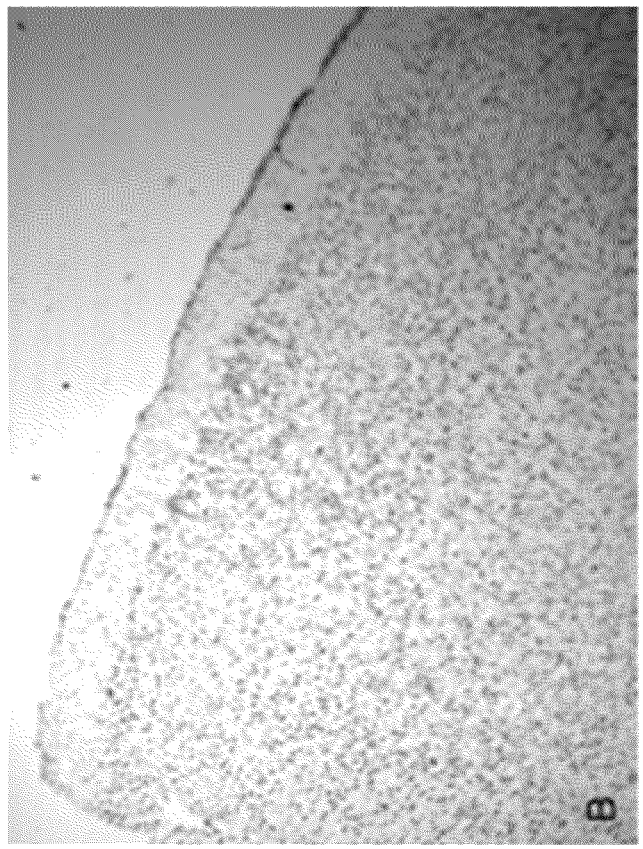
FIG. 5A-FIG. 5D are photomicrographs taken of the frontal cortex stained with cresyl violet from two Han-Wistar rats, 10 days post-TBI from 5.0 bar acoustic wave.
Figure 5A:
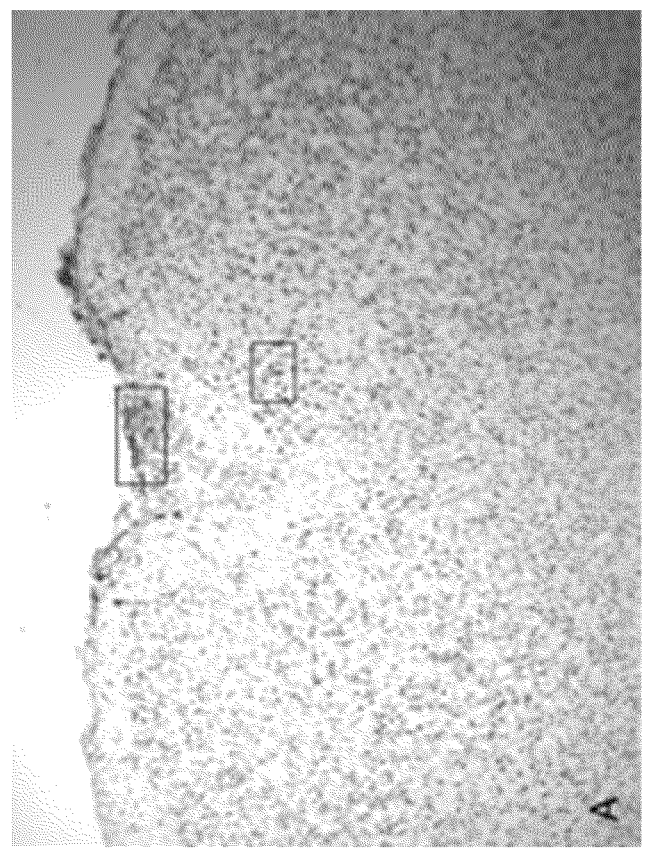

FIG. 5A shows the TBI-targeted left frontal cortex 10 days after 5.0 bar acoustic wave treatment. Note the severely damaged cortex compared to 3.4 bar treatment cortex (see FIG. 4A and FIG. 4C). While the histology from the 3.4 bar treatment revealed moderate impairment of the dura mater and the arachnoid layer, the 5.0 bar treatments showed significantly more damage to post-TBI tissue that ranges well beyond the pia mater. The intact contralateral cortex showed no apparent damage (FIG. 5B). Also, no additional damage was detected in any other brain region of the TBI-treated rats, including the hippocampus.

Figures 5C, 5D:
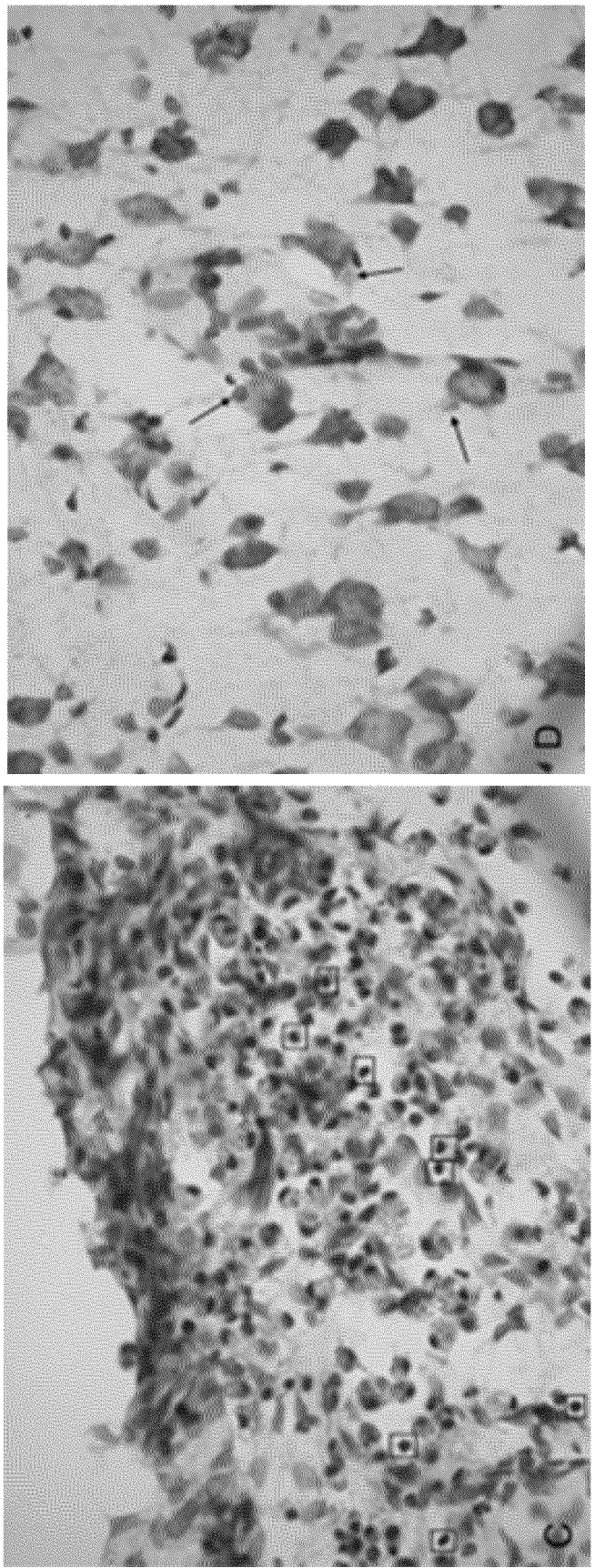

FIG. 5C and FIG. 5D are higher magnification photomicrographs taken from the highlighted regions of FIG. 5A (FIG. 5C upper region, FIG. 5D lower region of FIG. 5A). FIG. 5C shows the damage taken from the damaged impact zone at the top of the infarct. Very few intact pyramidal neurons remain in this region. Notice the lightly stained granulated cells that appear to be leukocytes infiltrating from capillaries due to disruption of the blood-brain barrier. FIG. 5D shows the continuation and persistence of damaged cells throughout the parenchyma of the infarct region with the arrows showing granulated cells. These cells are likely macrophages that have phagocytized blood products or other injured cells. Large reparative astrocytes and condensed dark cells can be seen in FIG. 5D as well.

Figure 6A:
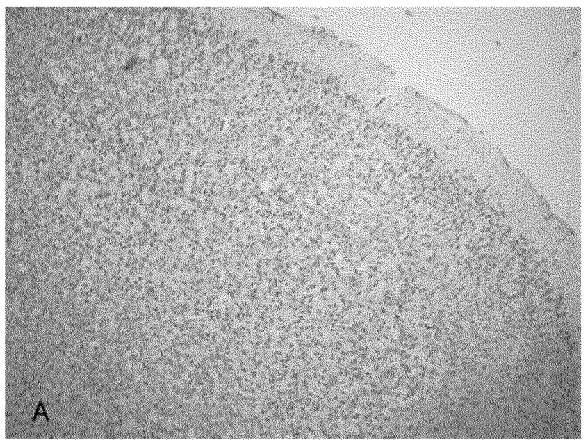
FIG. 6A-FIG. 6D are photomicrographs taken of the frontal cortex showing the overall depth of injury due to the penetration of acoustic waves: the control (0 bar), 3.4, 4.2, and 5.0 bar TBI, respectively of Han-Wistar rats, ten days post-injury.
Figure 6B:
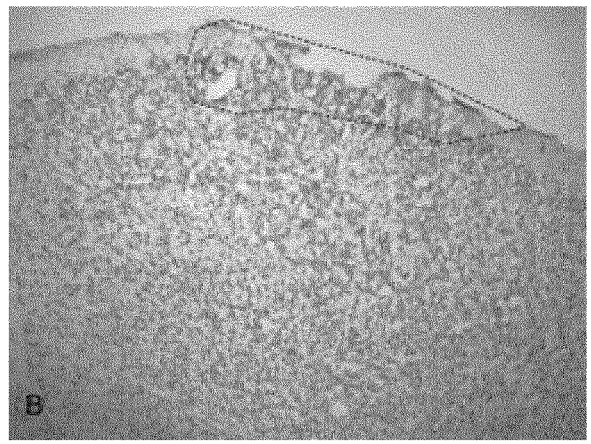
Figure 6C:
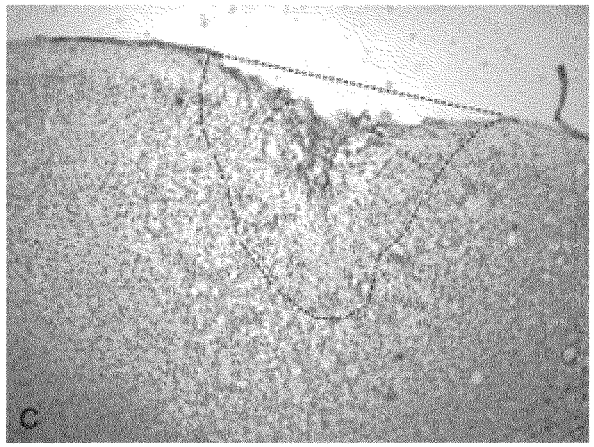
Figure 6D:
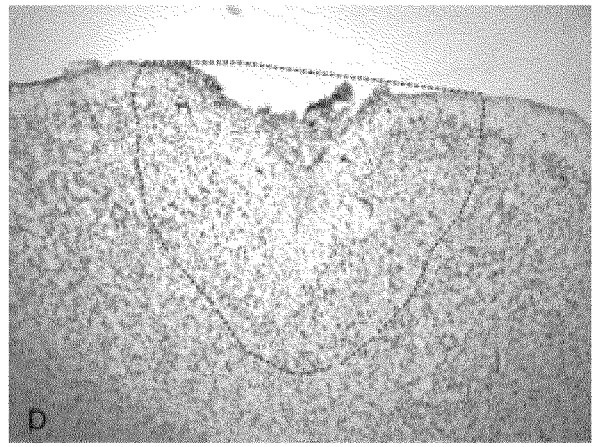

A side-by-side comparison of all four treatments is shown in FIGS. 6A-6D. An intact, uninjured cortex revealed no detectable damage (FIG. 6A). Slight damage of the outer cortex that does not penetrate beyond the pia mater is seen in the 3.4 bar treatment (FIG. 6B). The injury from the 4.2 bar treatment is much more significant than that of the 3.4 bar, penetrating beyond the pia mater and reaching cortical neurons (FIG. 6C). The depth of the 4.2 bar injury can be compared to that of the 5.0 bar injury (FIG. 6D). The 5.0 bar treatment is much more pervasive and penetrates even deeper into the cortex. The clearer space within the marked region (FIG. 6D) clearly shows neuronal cell death.

Figure 7:
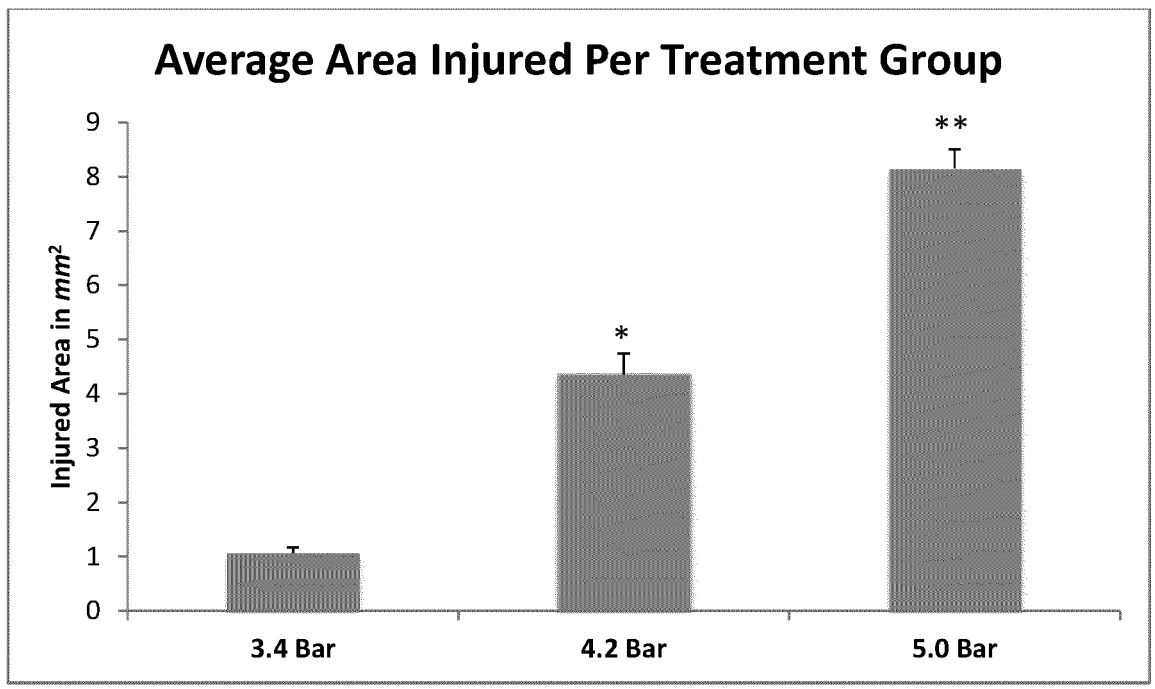
FIG. 7 is a chart showing the average area injured per treatment group. Quantitative measurements of the TBI injured area ($mm^2$) from Han-Wistar rats (n=10 for all treatments) subjected to acoustic wave treatments at 3.4, 4.2, and 5.0 bar. Quantification of the TBI infarct area was determined by the disruption of cells including the condensed dark cells which extend out to the periphery of the recovering border of the injury. The damaged cortical area surrounding the TBI was then traced by following the boundary of these peripheral cells. The infarct area was then quantified using SketchandCalc™ to measure the region of damage ($mm^2$). An ANOVA showed statistical differences among the treatment groups (F=134.9; p<0.001, denoted * and **) in a dose-dependent manner. All values are means±standard error.

The depth of TBI-induced injury was analyzed from the tissue slices from the 3.4, 4.2, and 5.0 bar treatment groups. The damaged cortical area from each animal was traced and outlined (see FIGS. 6B-6D), and a mean injured area was determined (FIG. 7). The 3.4 bar treatment group had an average injury area of 1.07 mm$^2$. The 4.2 bar treatment group had an average injury area of 4.36 mm$^2$—nearly four times greater than the damage caused by the 3.4 bar treatment. Finally, the 5.0 bar treatment group had an average injury area of 8.15 mm$^2$ which was nearly eight times greater than the 3.4 bar and nearly two times greater than the 4.2 bar injury. An ANOVA showed statistical differences among the treatment groups (F=134.90; $p<0.001$) in a dose-dependent manner.

Experimental Findings

These results demonstrate that the presently disclosed systems and methods of generating an acoustic wave TBI fulfill the criteria for behavioral, neuropathological, and histological outcomes involved in mild traumatic brain injury (TBI) similar to damages observed in other animal TBI models. The present technique can be highly reproducible in the areas of behavioral response, motor skills, memory analysis, and tissue damage. The acoustic wave TBI can be a closed skull model, in some embodiments, making it clinically advantageous to the development of potentially innovative treatments, including possible stem cell therapies (e.g., SVF stem cell therapy). Accordingly, the systems and methods of the present technology are useful in developing a veterinary model of TBI.

In the study, all acoustic wave TBI treatments were administered to the left frontal motor cortex, the area of the brain responsible for voluntary movement as well as memory and decision-making. Rats that received isoflurane anesthesia and sham-TBI treatment moved around from left to right equally upon waking and righting. Conversely, 100% of the experimental rats that received treatment regardless of the amplitude always rolled to their right (contralateral) side upon righting, confirming that the acoustic wave generated from the TBI device consistently administered the same severity of injury targeted to the same region of the cortex. The results were ultimately confirmed by histological analysis that showed that the acoustic-wave TBI technique can be highly reproducible.

Figure 2:
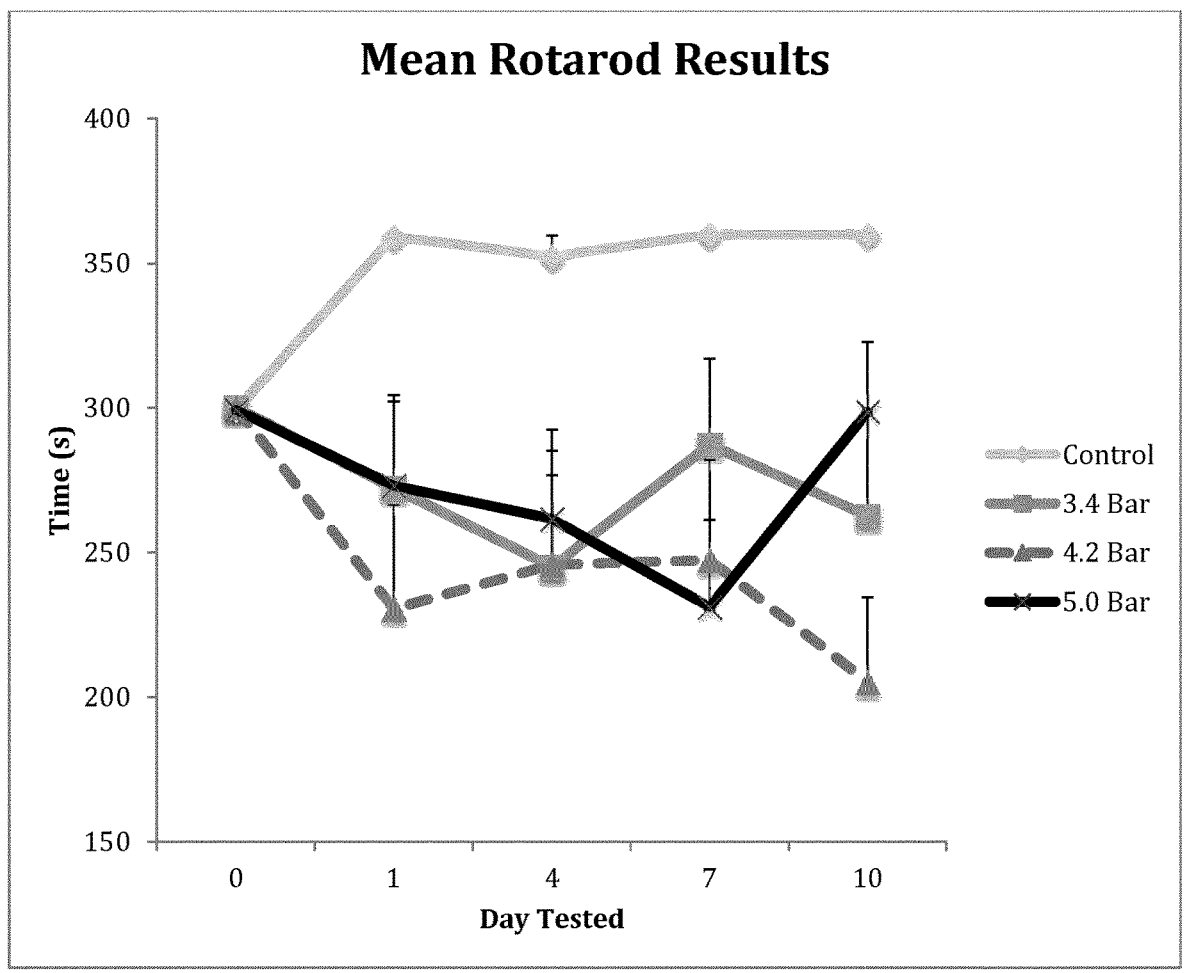
FIG. 2 is a graph showing the mean rotarod results. The rotarod test was performed to assess the decline in motor coordination of Han-Wistar rats after traumatic brain injury (TBI) treatment. The graph displays the mean time spent on the rotating bar (s) of control and TBI rats from Day 0 (prior to TBI treatment) to 10 days post-treatment. Treatments included control (0 bar), and experimental animals 3.4 bar, 4.2 bar, and 5.0 bar (n=10 for all treatments). The graph shows a significant decline in motor skills of TBI treated animals compared to controls (Repeated Measures ANOVA; F=5.01; p<0.005). All values are means±standard error.

In addition to the observation of a consistent righting response, the treated animals were also analyzed for motor skills and memory disturbances caused by acoustic wave TBI. FIG. 2 shows the variation between the control and the TBI test groups in the rotarod assay. Post-TBI analysis throughout the duration of the 10 days of testing showed that the control and TBI test groups differed by a significant, 20% reduction in the rotarod latencies ($p<0.01$). The results presented herein clearly indicate that the acoustic wave induced TBI resulted in substantial damage to the motor cortex at least over the ten-day test period.

Figure 3:
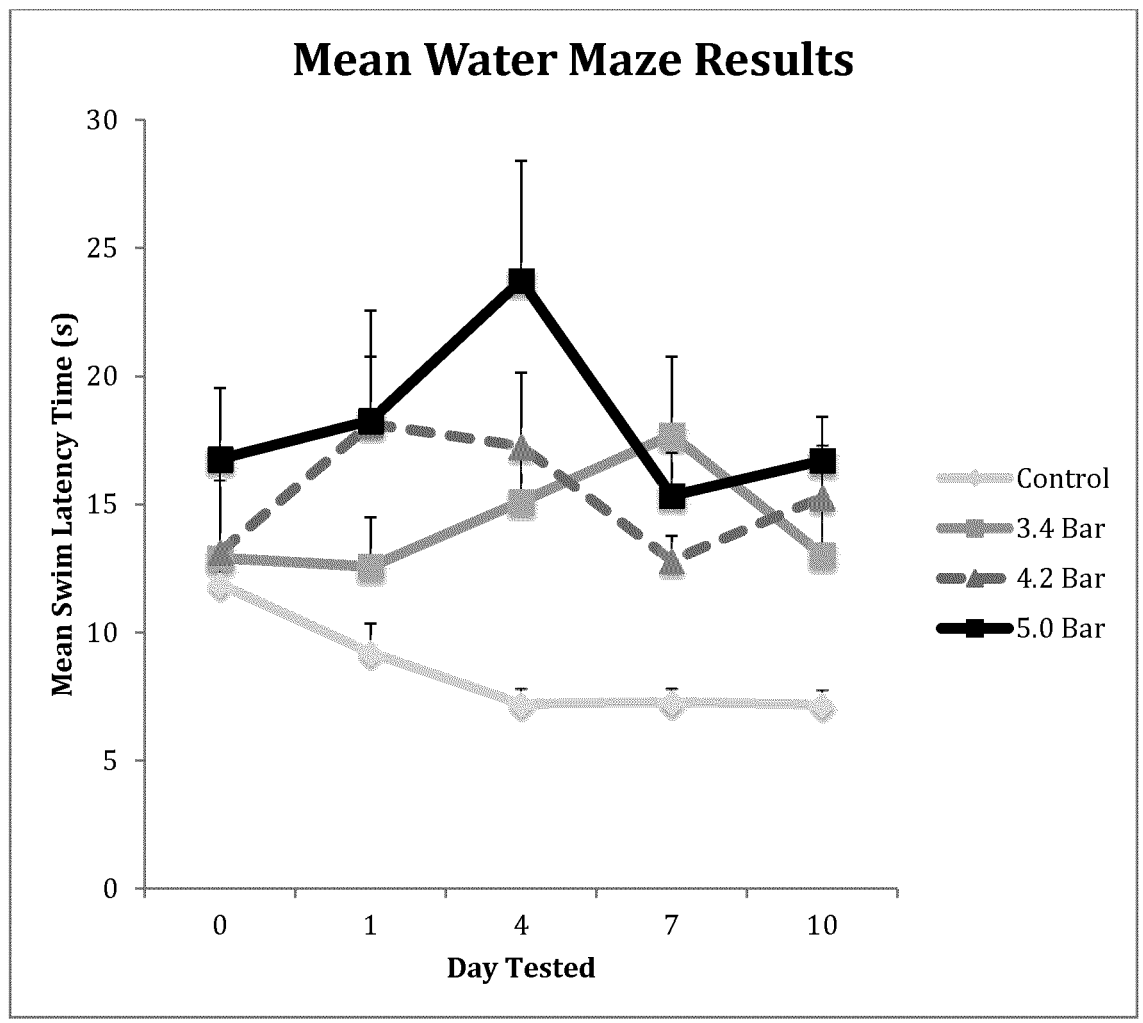
FIG. 3 is a graph showing the mean water maze results. The water maze was used to assess the spatial memory of Han-Wistar rats post-treatment compared to the control group. The graph displays the mean swim latency times of control and TBI rats from Day 0 (prior to TBI treatment) to 10 days post-treatment. Acoustic wave treatments included a control (0 bar), and experimental 3.4 bar, 4.2 bar, and 5.0 bar (n=10 for all treatments). The results indicate a significant increase in timed swim latency of TBI-treated animals compared to untreated controls (Repeated Measures ANOVA; F=2.80; p<0.05). All swim latency values are means±standard error.

Like the rotarod motor skills testing, similar significant trends were observed in the water maze assay. As shown in FIG. 3, first, a rapid initial decline in performance was seen followed by slight improvements, then declining again by the final day of testing. Specifically, a significant decline in memory recall was observed in rats that received TBI. The administration of TBI caused the 3.4 bar, 4.2 bar, and 5.0 bar groups to perform 37.2%, 38.1%, and 41.6% slower, respectively. In contrast, the control group improved their times by 39.6% by the final day of testing.

The amount of time an animal spends unconscious as a result of TBI may affect post-TBI memory and motor performance. Yet in the correlation study, no significant long-term effects of the anesthesia were observed, suggesting that the amount of time the rats remained unconscious due to the combined consequences of TBI and anesthesia may have no significant relationship to the animal's post-TBI memory or motor skills performance.

TBI is initially a vascular injury in nature as trauma causes damage to blood vessels that supply neural tissue with nutrients. The rupturing of the blood-brain barrier leads to inflammation, which is responsible for the headaches and dizziness in human patients. Accordingly, these initial effects may have caused the observed day 1 declines in rotarod and water maze performances compared to both their pre-TBI (day 0). Nonetheless, FIGS. 2 and 3 show the animals improving albeit slightly after the initial injury insult on and post-TBI day 4 and day 10 results. This post-TBI improvement may be due to the quick healing of the initial vascular injury, mitigating the headaches and dizziness often associated with TBI. While the initial vascular injury caused swelling, neurons were able to continue with a compromised nutrient supply that may have caused these cells to eventually die, resulting in the observed reduced motor skills and memory performances. This was evidenced by the histological analyses described herein.

Indentation and fragmentation of the surface of the frontal cortex was observed where the acoustic waves were administered and focused (FIGS. 4 and 5). The severity of the acoustic TBI may correlate with the acoustic wave intensity (see, e.g., FIGS. 6 and 7). FIG. 5C shows injured compacted neural cells, many of which appear condensed and dark. FIG. 5D shows the perimeter of the infarct area visualized by the condensed dark cells. The impact from the 5.0 bar treatment severely ruptured blood vessels in the dura mater and the subarachnoid space before penetrating down past the pia mater, evidenced by granular phagocytized blood cells or the remnants of neurons (dark cells), also seen in FIG. 5C. These images (FIG. 5C) show the presence of phagocytic leukocytes near the impact zone, illustrating that the force from the TBI fractured blood vessels and caused the blood-brain barrier to rupture at least temporarily. Mukherjee, et al. suggested that these observed macrophages have entered into the TBI infarct to phagocytize the newly entered blood cells which elicit a yellowish stain from ingested red blood cells (these cells do stain yellow in the original color photomicrographs). The upregulation of expressed cytokines may also attract the infiltration of neutrophils to aid in cellular repair but may also lead to further degradation of the blood-brain barrier.

The pervasive nature of the acoustic wave may be best observed beyond the initial point of impact. FIGS. 5A and 5B as well as FIGS. 5C and 5D show the difference in the neuronal cells on the impacted side (FIGS. 5A, 5C, and 5D) and non-impacted side (FIG. 5B) 10 days after TBI. The cells from the damaged, left cortex are enlarged, and appear to be more disorganized and skewed than comparable cells in the right hemisphere. There are many hypertrophic astrocytes that have moved in to help repair the vascular brain injury, a sign of the increased severity of the injury.

The increasing size of the TBI may be dependent on acoustic wave intensity and can be observed in FIGS. 6 and 7, implicating the scalable nature of the Storz-D-Actor acoustic wave to produce a mild TBI (FIG. 6B) or a more intense moderate TBI (FIG. 6C, 6D). Accordingly, the Storz-D-Actor may produce a more severe TBI with repeated applications, resulting in much greater cell death. In some embodiments, the acoustic wave may be generated by a different device. While disruption and fragmentation of the dura mater seemed consistent throughout the test groups, wave intensity correlated to both the size and depth of TBI (FIGS. 6 and 7). Subsequent measurements of TBI infarct area (FIG. 7) corroborate the visual evidence in the photomicrographs. TBI injury causes pyknosis, defined as when neurons condense and become darkly stained cells. Other studies have observed similar results with dark neurons expressing apoptotic proteins Bax, BCl2 and cleaved caspase-3. Other experiments have identified the presence of jellyfish microglia that are activated after TBI insult and are part of the inflammatory process responsible for neuroprotection and reparative are cells, aiding in neuronal recovery.

The histological and behavioral results from the dose-response experiment advocate the applicability of an acoustic wave-induced TBI. Beyond invasive TBI models that utilize craniotomies, current closed-skull TBI models generally require subsequent blunt force trauma to the brain. Fragmentation and disruption of the outer cortex beyond the pia mater were observed in these studies. Such traumas have been shown to damage and kill neuronal tissue. Similarly, the acoustic wave generated by the Storz D-Actor illustrates identical histological effects (dying neurons, macrophages, astrocytes, etc.) previously seen in other TBI models. In addition, TBI models consistently exhibited many damaged neurons manifesting as dark cells. As the intensity of the acoustic wave increased from 3.4 bar to 5.0 bar, so did the number of observable dark neurons, consistent with the other blast intensity and controlled cortical impact TBI studies. Finally, sheering of the cortex tissue and opening the blood-brain barrier, appeared to recruit macrophages that have phagocytized blood products to the region, which has been also seen in fluid percussion injury models.

The behavioral results observed in the rotarod test were also comparable to previous studies that showed behavioral delinquencies immediately post-TBI and often depicted delayed setbacks in return to testing baselines one-week post-TBI. In addition, TBI rats that performed the water maze memory test displayed delays of 5-15 s in finding a hidden platform compared to control rats. Different TBI methods also revealed significantly increased swim latency times following TBI, taking a period of days to weeks to fully recover to baseline. Although the hippocampus was not directly impacted during this study, it has been suggested that damage to the prefrontal cortex can result in increased swim latency. Also, sleep patterns essential to memory formation and retention can be affected by a TBI, possibly causing increased swim latencies.

Conclusion

The results presented herein serve to validate the systems and methods of the present technology for generating TBI that could be easily used on animal models in a laboratory setting. Many researchers have used invasive craniotomies in inducing multiple kinds of brain injuries. The craniotomy methods alone can induce various unintended consequences and make it difficult to establish proper controls in such studies. By using the acoustic wave technology of the present technology, as demonstrated by the results presented herein, a TBI can be established in an animal model that avoids damage to the bony skull itself, and instead focuses the insult energy on a specific region of the frontal cortex. Ultimately, the presently disclosed acoustic model more accurately represents many of the TBI injuries, including the bTBI that military personnel receive at war, a TBI caused by overpressure from a nearby explosion in which no skull fracture is observed. Since the physiology of a bTBI and regular TBI are similar in terms of symptoms and histology, this presently disclosed model can be used to study TBI sustained in other concussion models, including vehicle collisions, falls, and athletics (football, boxing, soccer, and hockey).

Example 2: Animal Model for Stromal Vascular Fraction (SVF) Treatment of Acoustic Wave Induced Traumatic Brain Injury (TBI)

This example demonstrates that the systems and methods of the present technology are capable of inducing a closed-head brain trauma animal model of traumatic brain injury (TBI) that allows for the analysis of stem cell therapy.

Materials and Methods

Rowett Nude Rat (RNU). This experiment was performed using 95-100 day old male Rowett Nude immunosuppressed rats (RNUs). Rats were taken from an RNU rat colony maintained at California State University Northridge. Three RNU groups (n=18 total) were tested in this experiment. All animals received a TBI on day 0. Immediate Group (n=6) received a 0.5 ml tail vein injection of SVF shortly after TBI on day 0.72 Hour Group (n=6) received a 0.5 ml tail vein injection of SVF at 3 days post-TBI. Control Group (n=6) received a 0.5 ml tail vein injection of only lactated Ringer's solution on day 0 immediately post-TBI. All animals underwent the same behavioral testing on 3 nonconsecutive days, beginning 5 days prior to TBI. All protocols utilized in this study were approved by California State University, Northridge's Institutional Animal Care and Use Committee (IACUC).

TBI Induction. The Storz-D-Actor, commonly used in orthopedic, urology, cardiology, and aesthetic medical practices, was used to induce a closed head blast TBI. The device emits an acoustic wave which penetrates the skull and causes neural damage similar to that of a mild to moderate TBI.

Each RNU rat was anesthetized with 2.5% isoflurane mixed in 02 for 45 seconds before receiving a TBI. Each RNU rat received a single pulse of acoustic wave energy that was emitted at 5.0 bar from the Storz-D-Actor. The pneumatic hand-held device was held constantly posterior to the rat's left eye so that the acoustic wave was directed to the left frontal motor cortex of the brain. Immediately after the TBI was induced, rats were rolled onto their backs, and the time it took to right themselves was recorded.

Stromal Vascular Fraction Treatment. The SVF for this research was obtained from the Cell Surgical Network that received consents from anonymous patients who had been previously cleared of any blood borne disease. To extract the SVF, patients received local sub-dermal anesthetic, and a mini-liposuction was performed. After extraction of the adipose tissue, the cells were incubated in a closed sterile container with GMP grade collagenase (Roche) for enzymatic digestion of the constricting extracellular matrix. A Time Machine™ centrifuge (Medikan International, Kangnam, South Korea) to isolate the SVF in accordance with Cell Surgical Network standard protocol.

The cells in the SVF were first counted using the Invitrogen Cell Countess I to obtain an estimated count prior to flow cytometry analysis. Hematopoietic stem cells (HSCs) were identified by $CD45^+$, $DC34^{low}$, $CD14^+$, and $CD31^-$ cell surface markers. Adipose derived stem cells (ASCs) were identified by $CD45^-$, $CD34^+$ and $CD90^+$ cell surface markers. After the SVF was harvested, the cells were incubated with Qtracker 625 cell labeling materials in RPMI media on the same day. Once the cells were prepared with Q-Dots and incubated for 2 hours, approximately 500,000 stromal vascular fraction cells were suspended in 0.5 ml of lactated Ringer's solution and placed into 1 ml sterile syringes. The freshly harvested and isolated SVF was delivered via tail vein injection to all TBI experimental animals within a 5 hour window. Negative control TBI rats received lactated Ringer's via tail vein injection at the same time as their experimental pairs.

Figure 8A:
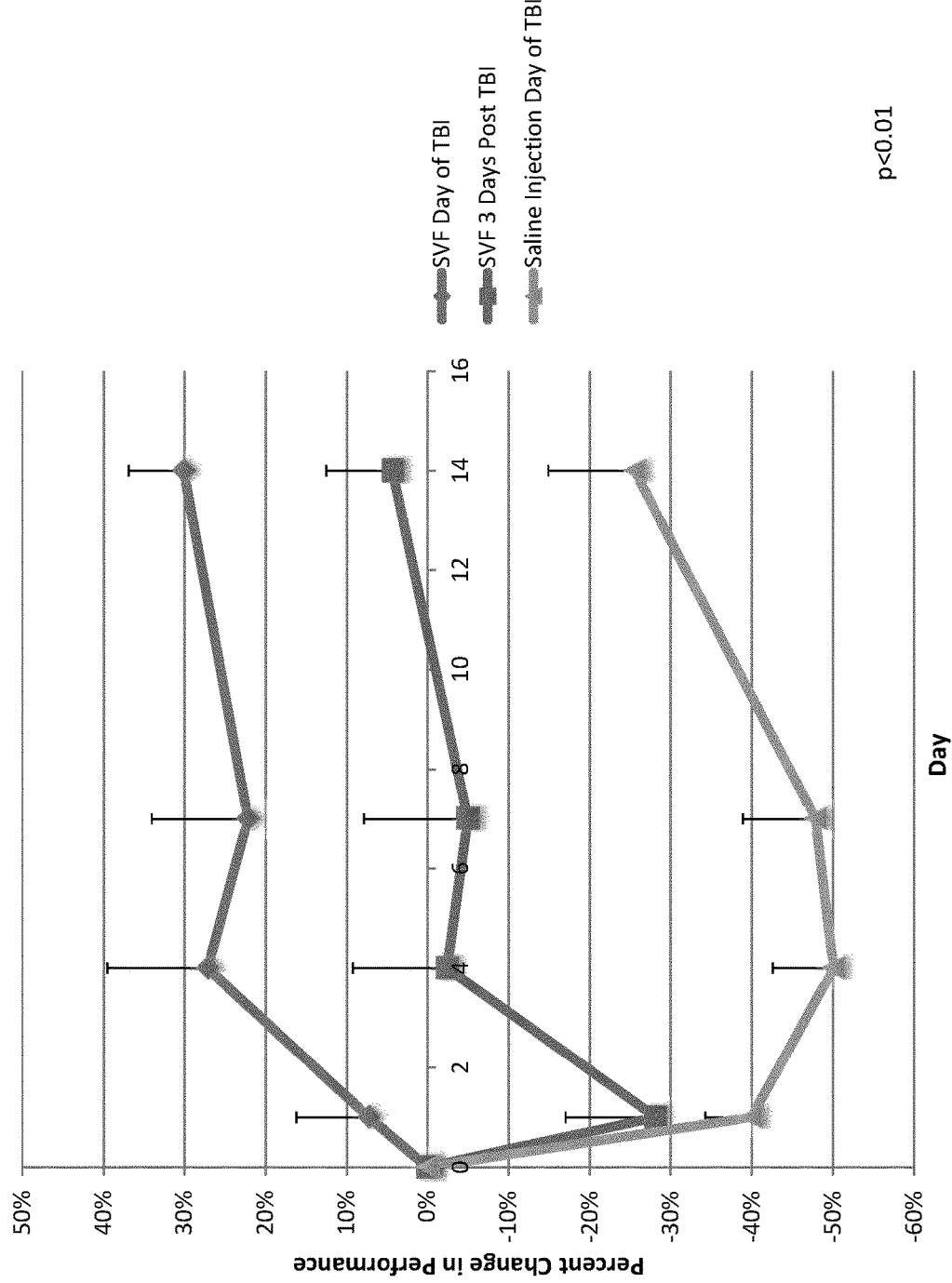
FIGS. 8A and 8B are charts showing the effects of stromal vascular fraction (SVF) treatment on motor skills (FIG. 8A) and memory (FIG. 8B).

Rotarod Test. To test for motor coordination impairment, all animals underwent three nonconsecutive days of rotarod training, five days prior to the administration of TBI. The animals were trained on the rotarod (Med Associates Inc., St. Albans, Vt.), which increased in speed from 4 to 40 rpm over the course of 300 seconds. On training days (including one hour prior to TBI induction) and testing days (post-TBI), the animals performed the test three times, and their rotarod results were averaged. On the final day of training (day 0), the animals were left on the rotarod as long as possible to record their maximum performance capability or which was used as baseline to compare post-TBI performance. Their post-implant, rotarod performances were tested on 1, 4, 7, and 14 days post-TBI. Each animal's rotarod latency times were compared to their individual baseline performance and used to determine percentage of peak performance (FIG. 8A).

Figure 8B:
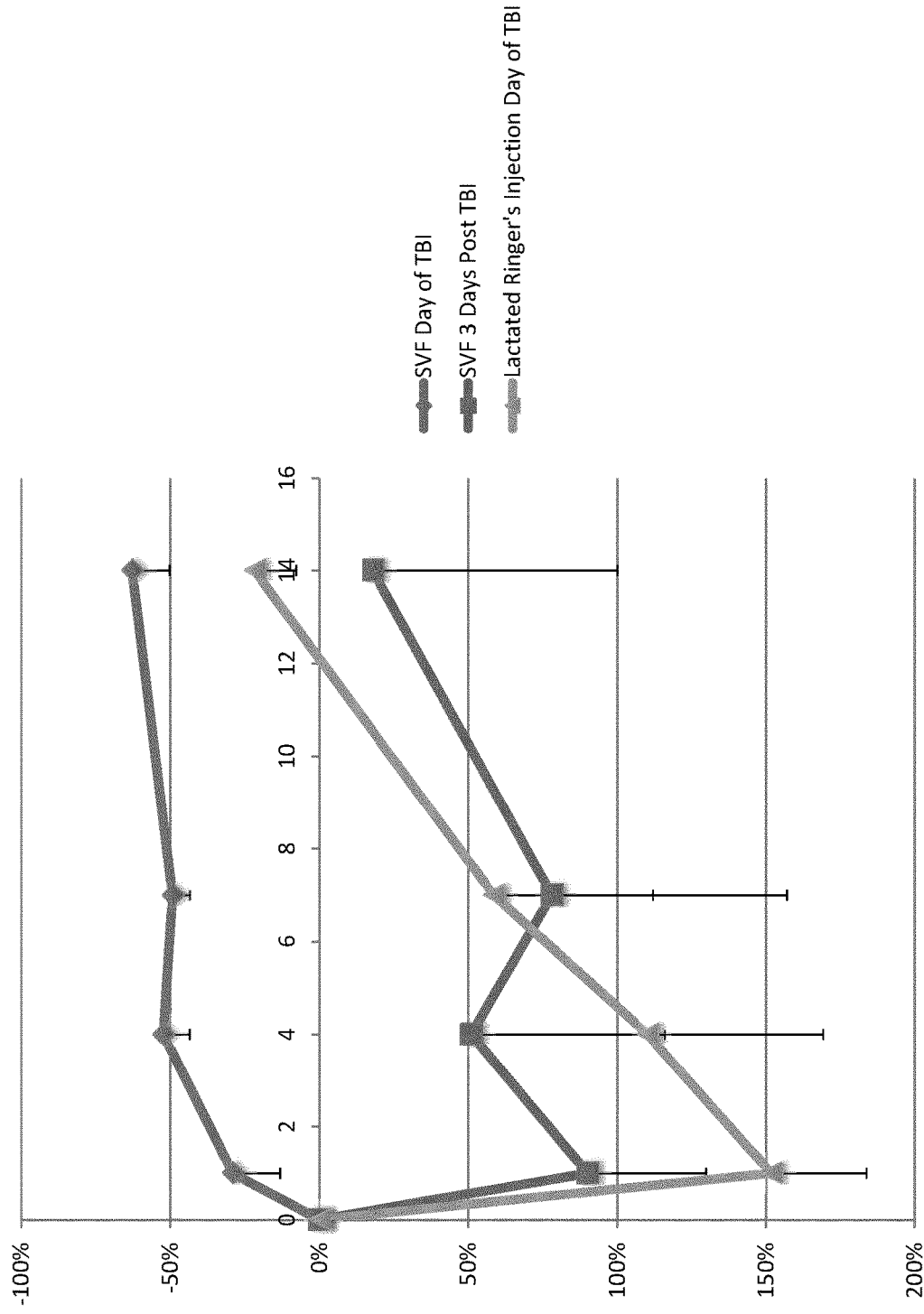

Morris Water Maze Test. To test for memory impairment, we utilized a water maze. A round black plastic tub (one meter diameter) was divided into four quadrants and filled (20 cm) with tap water. The water (18°±1° C.) was made opaque by using dehydrated milk powder. Above the water line, each quadrant was marked with unique, orienting white tape. A glass platform (5 cm diameter) was always placed in the same location, 2.5 cm below the waterline in the $3^{rd}$ quadrant. The rats were placed in the water facing away from the platform in the $1^{st}$ quadrant. The time (swim latency) it took for the rat to turn around, swim to the submerged platform and stand on top of it for at least a full second was recorded. Similar to the rotarod test, the animals underwent three nonconsecutive days of training in the water maze, starting five days prior to TBI induction. Three daily trials were completed with five minutes of rest in between each trial. Each water maze test was conducted after completion of rotarod testing. After TBI induction, animals were retested on days 1, 4, 7, and 14. Their swim latency times (seconds) were recorded for three nonconsecutive trials and averaged. Each animal's swim latency times were determined as a percentage of their baseline performance (taken one hour prior to TBI administration) (FIG. 8B).

Histology. Fourteen days post-TBI administration after the final behavioral assays were run, all animals were injected IP with 400 mg/kg chloral hydrate. The animals were transcardially perfused and fixed with 4% paraformaldehyde dissolved in 0.1 M phosphate buffered solution (PBS). Their brains were removed, and post-fixed in 4% paraformaldehyde/0.1M PBS for 48 hours at 4° C. The fixed brains were then placed in a solution of 20% sucrose in paraformaldehyde/0.1M PBS for an additional 48 hours (also at 4° C.) prior to sectioning. The frontal cortex was sliced on a cryostat on the coronal plane (25 μm thick) at the same stereological level for all animals. The tissue was arranged on a glass slide for drying, and then stained with cresyl violet.

Statistics. Statistical analyses were performed on data collections. Multiple comparisons of data collected from rotarod and water maze assays were analyzed by repeated measures ANOVA. All figures are displayed with means±SE bars.

Results

As shown in FIGS. 8A and 8B, the administration of SVF to the acoustic wave induced model of TBI improved both memory and motor skills functions. Accordingly, these results demonstrate that the TBI experimental model of the present technology provides a basis for analyzing stem cell therapeutics.

REFERENCES

The following references are incorporated by reference.
1. Langlois, J.; Rutland-Brown, W.; Wald, M. The epidemiology and impact of traumatic brain injury: A brief overview. *J. Head Trauma Rehabil.* 2006, 21, 375-378.
2. Kerr, Z. Y.; Harmon, K. J.; Marshall, S. W.; Proescholdbell, S. K.; Waller, A. E. The epidemiology of traumatic brain injuries treated in emergency departments in North Carolina 2010-2011. *NC Med. J.* 2014, 75, 8-14.
3. Meyer, P. G.; Ducrocq, S.; Carli, P. Pediatric neurologic emergencies. *Curr. Opin. Criti. Care* 2001, 7, 81-87.
4. Petraglia, A. L.; Dashnaw, M. L.; Turner, R. C.; Bailes, J. E. Models of mild traumatic brain injury: Translation of physiological and anatomic injury. *Neurosurgery* 2014, 75, S34-S49.
5. Raghupathi, R.; Graham, D. I.; Mcintosh, T. K. Apoptosis after traumatic brain injury. *J. Neurotrauma* 2000, 17, 927-938.
6. Babaee, A.; Eftekhar-Vaghefi, S. H.; Asadi-Shekaari, M.; Shahrokhi, N.; Soltani, S. D.; Malekpour-Afshar, R.; Bashi, M. Melatonin treatment reduces astrogliosis and apoptosis in rats with traumatic brain injury. *Iran. J. Basic Med. Sci.* 2015, 18, 867-872.
7. McKee, A.; Robinson, M. Military-related traumatic brain injury and neurodegeneration. *Alzheimers Dement.* 2014, 10, 242-253.
8. Beauchamp, K.; Mutlak, H.; Smith, W. R.; Shohami, E.; Stahel, P. F. Pharmacology of traumatic brain injury—where is the "golden bullet"? *Mol. Med.* 2008, 14, 731-740.
9. Malkesman, O.; Tucker, L. B.; Ozl, J.; McCabe, J. T. Traumatic brain injury—Modeling neuropsychiatric symptoms in rodents. *Front. Neurol.* 2013, 4, 157.
10. Wojcik, B. E.; Stein, C. R.; Bagg, K.; Humphrey, R. J.; Orosco, J. Traumatic brain injury hospitalizations of U.S.

army soldiers deployed to Afghanistan and Iraq. *Am. J. Prev. Med.* 2010, 38, 108-116.
11. Hoge, C. W.; McGurk, D.; Thomas, J. L.; Cox, A. L.; Engel, C. C.; Castro, C. A. Mild traumatic brain injury in U.S. soldiers returning from Iraq. *N. Engl. J. Med.* 2008, 358, 453-463.
12. Cristian, A. Blast-related mild traumatic brain injury: Mechanisms of injury and impact on clinical care. *Mt. Sinai J. Med.* 2009, 76, 111-118.
13. Marar, M.; McIlvain, N. M.; Fields, S. K.; Comstock, R. D. Epidemiology of concussions among United States high school athletes in 20 sports. *Am. J. Sports Med.* 2012, 40, 747-755.
14. Jorden, B. D. Chronic traumatic brain injury associated with boxing. *Semin Neurol.* 2000, 20, 179-185.
15. Cunon, V. A.; Putukian, M.; Boyer, C.; Dewttwiler, A. A diffusion tensor imaging study on the white matter skeleton in individuals with sports-related concussion. *J. Neurotrauma* 2001, 28, 189-201.
16. Namjoshi, D. R.; Good, C.; Cheng, W. H.; Panenka, W.; Richards, D.; Cripton, P. A.; Wellington, C. L. Towards clinical management of traumatic brain injury: A review of models and mechanisms from a biomechanical perspective. *Dis. Models Mech.* 2013, 6, 1325-1338.
17. Cernak, I. Animal models of head trauma. *Neurotherapeutics* 2005, 2, 410-422.
18. Alder, J.; Fujioka, W.; Lifshitz, J.; Crockett, D. P.; Thakker-Varia, S. Lateral fluid percussion: Model of traumatic brain injury in mice. *J. Vis. Exp.* 2011, 22, e3063.
19. Dixon, C. E.; Clifton, G. L.; Lighthall, J. W.; Yaghmai, A. A.; Hayes, R. L. A controlled cortical impact model of traumatic brain injury in the rat. *J. Neurosci. Methods* 1991, 39, 253-262.
20. Williams, A. J.; Hartings, J. A.; Lu, X.-C. M.; Rolli, M. L.; Dave, J. R.; Tortella, F. C. Characterization of a new rat model of penetrating ballistic brain injury. *J. Neurotrauma* 2005, 22, 313-331.
21. Ozen, I.; Boix, J.; Paul, G. Perivascular mesenchymal stem cells in the adult human brain: A future target for neuroregeneration? *Clin. Transl. Med.* 2012, 1, 30.
22. Flierl, M. A.; Stahel, P. F.; Beauchamp, K. M.; Morgan, S. J.; Smith, W. R.; Shohami, E. Mouse closed head injury model induced by a weight-drop device. *Nat. Protoc.* 2009, 4, 1328-1337.
23. Mishra, V.; Skotak, M.; Schuetz, H.; Heller, J.; Chandra, N. Primary blast cause mild, moderate, sever and lethal TBI with increasing blast overpressures: Experimental rat injury model. *Sci. Rep.* 2016, 6, 26992.
24. Friedland, D. Improving the classification of traumatic brain injury: The May classification system for traumatic brain injury severity. *Spine* 2013, doi:10.4172/2165-7939.54-005.
25. Xiong, Y.; Mahmood, A.; Chopp, M. Animal models of traumatic brain injury. *Nat. Rev. Neurosci.* 2013, 14, 128-142.
26. Shultz, S.; MacFabe, D.; Foley, K.; Taylor, R.; Cain, D. A single mild fluid percussion injury induces short-term behavioral and neuropathological changes in the Long-Evens rat: Support for an animal model of concussion. *Behav. Brain Res.* 2011, 224, 326-335.
27. Yu, S.; Kaneko, Y.; Bae, E.; Stahl, C.; Wang, Y.; van Loveren, H.; Sanberg, P.; Borlongan, C. Severity of controlled cortical impact traumatic brain injury in rats and mice dictates degree of behavioral defects. *Brain Res.* 2009, 1287, 157-163.
28. Mukherjee, S.; Zeitouni, S.; Cavarsan, C. F.; Shapiro, L. A. Increased seizure susceptibility in mice 30 days after fluid percussion injury. *Front. Neurol.* 2013, 4, 28.
29. Morehead, M.; Bartus, R. T.; Dean, R. L.; Miotke, J. A.; Murphy, S.; Sall, J.; Goldman, H. Histopathologic consequences of moderate concussion in an animal model: Correlations with duration of unconsciousness. *J. Neurotrauma* 1994, 11, 657-667.
30. Rinder, L.; Olsson, Y. Vascular Permeability changes in experimental brain concussion. *Acta Pathol. Microbiol. Scand.* 2009, 72, 350-352.
31. Beaumont, A.; Marmarou, A.; Hayasaki, K.; Barzo, P.; Fatouros, P.; Corwin, F.; Marmarou, C.; Dunbar, J. The permissive nature of blood brain barrier (bbb) opening in edema formation following traumatic brain injury. *Brain Edema XI* 2000, 76, 125-129.
32. Raghupathi, R.; Graham, D. I.; Mcintosh, T. K. Apoptosis after traumatic brain injury. *J. Neurotrauma* 2000, 17, 927-938.
33. Elliott, M. B.; Jallo, J. J.; Barbe, M. F.; Tuma, R. F. Hypertonic saline attenuates tissue loss and astrocyte hypertrophy in a model of traumatic brain injury. *Brain Res.* 2009, 1305, 183-191.
34. Budde, M. D.; Shah, A.; Mccrea, M.; Cullinan, W. E.; Pintar, F. A.; Stemper, B. D. Primary blast traumatic brain injury in the rat: Relating diffusion tensor imaging and behavior. *Front. Neurol.* 2013, 4, 154.
35. Ghadiri, T.; Sharifzadeh, M.; Khodagholi, F.; Mousavi, S. M. M.; Hassanzadeh, G.; Zarrindast, M.-R.; Gorji, A. A novel traumatic brain injury model for induction of mild brain injury in rats. *J. Neurosci. Methods* 2014, 233, 18-27.
36. Watts, L. T.; Long, J. A.; Chemello, J.; Koughnet, S. V.; Fernandez, A.; Huang, S.; Shen, Q.; Duong, T. Q. Methylene blue is neuroprotective against mild traumatic brain injury. *J. Neurotrauma* 2014, 31, 1063-1071.
37. Henninger, N.; Dützmann, S.; Sicard, K. M.; Kollmar, R.; Bardutzky, J.; Schwab, S. Impaired spatial learning in a novel rat model of mild cerebral concussion injury. *Exp. Neurol.* 2005, 195, 447-457.
38. Thompson, H. J.; LeBold, D. G.; Marklund, N.; Morales, D. M.; Hagner, A. P.; McIntosh, T. K. Cognitive evaluation of traumatically brain-injured rats using serial testing in the Morris water maze. *Restor. Neurol. Neurosci.* 2006, 24, 109-114.
39. Redish, A. D.; Touretzky, D. S. The role of the hippocampus in solving the Morris water maze. *Neural Comput.* 1998, 10, 73-111.
40. Kolb, B.; Sutherland, R. J.; Whishaw, I. Q. A comparison of the contributions of the frontal and parietal association cortex to spatial localization in rats. *Behav. Neurosci.* 1983, 97, 13-27.
41. Cole, J. T.; Yarnell, A.; Kean, W. S.; Gold, E.; Lewis, B.; Ren, M.; Mcmullen, D. C.; Jacobowitz, D. M.; Pollard, H. B.; O'Neill, J. T.; et al. Craniotomy: True sham for traumatic brain injury, or a sham of a sham? *J. Neurotrauma* 2011, 28, 359-369.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a nonlimiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method of simulating closed-skull traumatic brain injury (TBI) in a closed-skull non-human animal model, the method comprising administering one or more acoustic waves to the brain of the closed-skull non-human animal with an acoustic wave generator, thereby resulting in brain trauma.

2. The method of claim 1, wherein a single acoustic wave is administered to the brain of the animal.

3. The method of claim 1, wherein the acoustic wave is administered at a pressure of 1.0-5.0 bar.

4. The method of claim 1, wherein the acoustic wave is administered to one or more brain regions.

5. The method of claim 4, wherein the brain region is the frontal motor cortex.

6. The method of claim 1, wherein the non-human animal exhibits one or more of impaired cognitive function or impaired motor coordination resulting from the brain trauma.

7. The method of claim 1, wherein the non-human animal model is a rodent.

8. A closed-skull non-human animal model of closed-skull traumatic brain injury (TBI), wherein one or more acoustic waves are administered to the brain of the closed-skull non-human animal with an acoustic wave generator, and wherein the one or more acoustic waves induces brain trauma.

9. The non-human animal model of TBI of claim 8, wherein a single acoustic wave is administered to the brain of the animal.

10. The non-human animal model of TBI of claim 8, wherein the acoustic wave is administered at a pressure of 1.0-5.0 bar.

11. The non-human animal model of TBI of claim 8, wherein the acoustic wave is administered to one or more brain regions.

12. The non-human animal model of TBI of claim 11, wherein the brain region is the frontal motor cortex.

13. The non-human animal model of TBI of claim 8, wherein the non-human animal model is a rodent.

14. The non-human animal model of claim 8, wherein the animal exhibits cognitive impairment resulting from the brain trauma.

15. The non-human animal model of claim 8, wherein the animal exhibits impaired motor skills resulting from the brain trauma.

16. A system comprising an acoustic wave generator configured to produce one or more acoustic waves resulting in brain trauma in a closed-skull non-human animal when the one or more acoustic waves are administered to the brain of the closed-skull non-human animal.

17. The system of claim 16, wherein a single acoustic wave is administered to the brain of the animal.

18. The system of claim 16, wherein the one or more acoustic waves is administered at a pressure of 1.0-5.0 bar.

19. The system of claim 16, wherein the one or more acoustic waves is administered to one or more brain regions.

20. The system of claim 19, wherein the brain region is the frontal motor cortex.

* * * * *